United States Patent [19]

Golub

[11] Patent Number: 4,728,291

[45] Date of Patent: Mar. 1, 1988

[54] CLOTH WRAP DENTAL PROCESS

[76] Inventor: Jeff E. Golub, 128 E. 71st St., New York, N.Y. 10021

[21] Appl. No.: 878,640

[22] Filed: Jun. 26, 1986

[51] Int. Cl.$^4$ ................................................. A61C 5/00
[52] U.S. Cl. .................................. 433/215; 433/202.1; 433/223
[58] Field of Search ...................... 433/223, 222.1, 219, 433/218, 217.1, 215, 202; 264/16, 19, 20

[56] References Cited

U.S. PATENT DOCUMENTS

| | | | |
|---|---|---|---|
| 2,793,436 | 5/1957 | Gotlib | 264/20 |
| 3,974,567 | 8/1976 | Ridgeway | 433/217.1 |
| 4,392,829 | 7/1983 | Tanaka | 433/222.1 |
| 4,433,960 | 2/1984 | Garito et al. | 433/215 |

OTHER PUBLICATIONS 0269249, 7/1943, APC, Weikel.

Primary Examiner—Gene Mancene
Assistant Examiner—Adriene J. Lepiane
Attorney, Agent, or Firm—James P. Malone

[57] ABSTRACT

The process of reshaping a tooth comprising the steps of: applying a fabric to the tooth; bonding the fabric to the tooth; sculpting the bonded material; polishing and finishing the bonded material, wherein the fabric or cloth is silk or nylon.

3 Claims, 7 Drawing Figures

CLOTH WRAP DENTAL PROCESS

TECHNICAL FIELD

This invention relates to a process of enhancing the external fixation of bonding resin for reshaping teeth.

BACKGROUND AND PRIOR ART

Composite bonding resins can fracture. Unhappily, sometimes it is yesterday's bonding. But some bonding resins placed in the mouth 7, 10 or 14 years ago, though not always color stable, are still intact. This mystery has traditionally been answered by focusing on case selection; the resins have fared far better in low-stress areas. Resins placed in areas which overstress their tensile abilities will fail. Those of us who style smiles and are continually attempting to lengthen, widen and rotate teeth with composite materials have faced artistic and technical limitations. Cantilevering composites has been an anathema. Since these filled resins have no continuous internal matrices, they absorb stress almost entirely at the points of impact. Hence the more your composite resin hangs off the side of the tooth, the more the practitioner is out on a limb. If the patient is additionally a bruxer, the restoration will fail.

Buonocare, Jordan, Gwinnett, Pollack and others have described the properties and limitations of microfills, macrofills and hybrid bis-GMA resins. Clinicians have devised techniques to minimize the fracture of cantilevered composite resin, including, (1) over-relieving interferences in protrusive and lateral excursions, (2) rounding sharp line angles of the enamel structure, (3) utilizing as much enamel surface as possible for adhesion, (4) roughening the tooth surface with abrasive diamond stones before etching (Goldstein, Black), (5) insuring that the etchant and bonding adhesive is wrapped into the interproximal areas (Hendell), (6) using macrofills for the majority of the buildup and microfills only for the final outer surface. Still, bonding has had its limitations. Teeth which have needed to be lengthened or widened considerably, such as openbite cases or malformed, retruded or malposed teeth (and of course missing teeth) have always required conventional crowns and conventional bridges. Even Maryland Bridges have necessitated some form of metallic frame, and therefore, laboratory intervention.

THE INVENTION

The present invention provides a new and different process for enhancing the external fixation of bonding resin. Applicant has developed a new procedure, the Dental Cloth Wrap. Much like manicurist's nail extension, pieces of cloth are applied to the tooth, creating a matrix for additional bonding resin. Applicant has experimented with cotton, nylon, dacron and other synthetics; silk and nylon seem to work best. Silk, a proteinacious substance, has more little barbs than synthetic fibers for grabbing the resin. It is less rigid and therefore, more workable than cotton. As long cloth fibers are internalized within the ultimate composite resin, any fiber will probably be better than none. Applicant prefers either China Silk or the twenty gauge silk used by silk screeners. The most useful colors are ivory, beige and white.

OBJECTS OF THE INVENTION

A principal object of the invention is to provide a new and improved process for enhancing the external fixation of bonding resin.

Another object of the invention is to provide a new and improved process for enhancing the external fixation of bonding resin, in the process of reshaping a tooth comprising the steps of: applying a fabric to the tooth, bonding the fabric to the tooth, sculpturing the bonded material, polishing and finishing the bonded material for cosmetic and utilitarian purposes.

Another object of the invention is to provide a new and improved dental process, the process of reshaping a tooth comprising the steps of applying a fabric to the tooth, bonding the fabric to the tooth, sculpturing the bonded material, polishing and finishing the bonded material, applying orthodontic wax to approximate and mock-up the final restorations. A study model of the waxed mock-up is optional. The cloth will extend to within ½ mm of the final bonded length.

BRIEF DESCRIPTION OF THE FIGURES

These and other objects of the invention are apparent by the following specification and figures of which.

BEST MODE OF THE INVENTION

The Process is as follows

Figure 1:
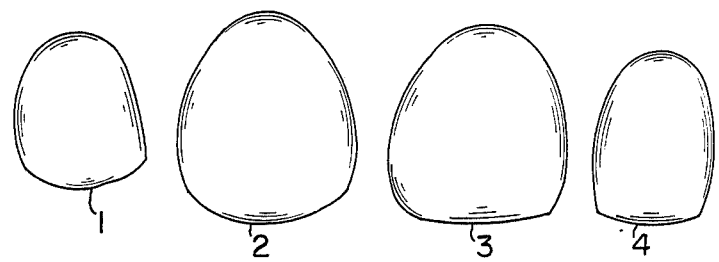
FIG. 1 is a front view of teeth to be enhanced by the present process.

1. After selecting an appropriate case, use soft orthodontic wax to approximate and mock-up the final restorations. A study model of the waxed mock-up is optional. The cloth will extend to within ½ mm of the final bonded length.

2. Pumice the teeth, etch them on all surfaces, then use standard lavage and drying techniques.

3. Cut the cloth in ½ inch lengths measured as wide as the proximal incisal corners (less about ½ mm from each edge). Cut two for each tooth and hold aside. Affix the cloth about half way up the tooth even for a 1 or 2 mm extension. For bruxers, even the tiniest extension requires a cloth wrap. The fabric ribbons can actually be any length. You will cut the incisal excess later.

4. Apply the light-cured bonding liquid to the enamel surface and cure.

5. Mix a non-light cured luting agent. Remember that the cloth fibers are opaque. Chemically cured Concise, Comspan, Micro-join and Super C, all commercially available, have all been used with good results.

6. Place a cellophane strip loosely adjacent to the lingual surface wrapping labially through the two interproximals. Place the auto-cured adhesive paste on the lingual enamel and onto the sides. Wet the cloth strip thoroughly with paste. Compress the parts together with the strip insuring that the extended silk is following the imaginary inclined plane of the ligual surface of the tooth. Remove any paste adhesive which spills onto the labial surface.

7. Optionally, place a bonding resin, preferably a macro-type, at the incisal edge and slightly onto the labial surface to fill in the space.

8. Now apply a new mix of adhesive paste on the labial enamel and on a second piece of cloth. Compress again with a clear plastic strip against the hardened lingual cloth-resin complex.

9. Once set, reduce the fabric-resin structure with a dry medium diamond stone to within ½ millimeter of the ultimate bonded length and width. Check the occlusion.

10. Roughen any fabric-resin material which appears shiny and add light cured bonding adhesive to the silk structrure and to the remaining enamel surface and cure it.

11. Add the composite resin, choosing a macrofill for the lingual surface for strength and a microfill for the labial surface for polish and luster.

12. Sculpt and finish as you would normally. The outer bonding composite resin should envelope the cloth entirely and should be firmly attached to the labial, lingual and proximal enamel surfaces, as well as the cloth-resin complex.

13. Polish and finish

The present invention has been successfully tested. It is essential for bruxers, for extending short teeth in open bite cases, for closing extra-large diastemas, especially in lower teeth where the proximal stress is higher, for periodontal splinting, for Manhattan bridges and for teeth in crossbite.

Advantages of Silk to Wrap Teeth
1. Silk cloth has exceptional tensile properties.
2. Silk in combination with a macro-resin produces a complex of unusual strength and durability.
3. Silk, a natural substance, is generally non-allergenic.
4. Silk can be fabricated in many colors.
5. Silk does not exercise undue water absorption properties.
6. Silk cloth has tiny microscopic barbs for grabbing the bonded resin.

The Present Dental Cloth Wrap Technique Can Be Used To
1. Widen teeth in preparation for bonding resin or laminates.
2. Lengthen teeth in preparation for bonding resin or laminates.
3. Reinforce weak teeth in preparation for bonding resin or laminates.
4. Rotate teeth in preparation for bonding resin or laminates.
5. Change teeth in crossbite in preparation for bonding resin or laminates.
6. Replace teeth in preparation for bonding resin or laminates.
7. Opaque teeth in preparation for bonding resin or laminates.
8. Splint loose teeth.
9. Reinforce temporary crowns and bridges.
10. Reinforce composite crowns.
11. Enable Manhattan composite bridges.

More specifically, FIG. 1 shows a set of teeth, 1, 2, 3, 4, which are short and to be lengthened by the present process.

Figure 2:
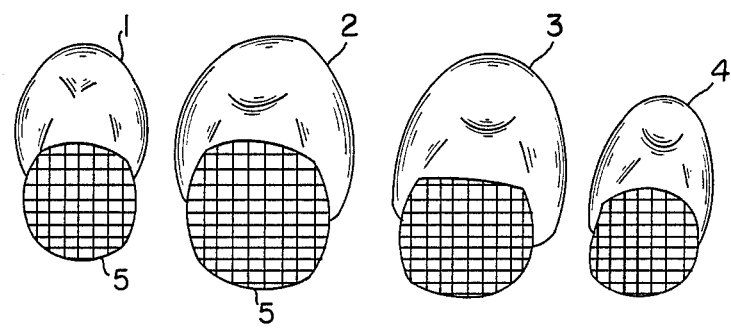
FIG. 2 shows a front view of fabric-resin complex placed on the lingual surfaces of the teeth.

FIG. 2, shows a fabric-resin complex 5, placed on the lingual surfaces of the teeth, 1 to 4.

Figure 3:
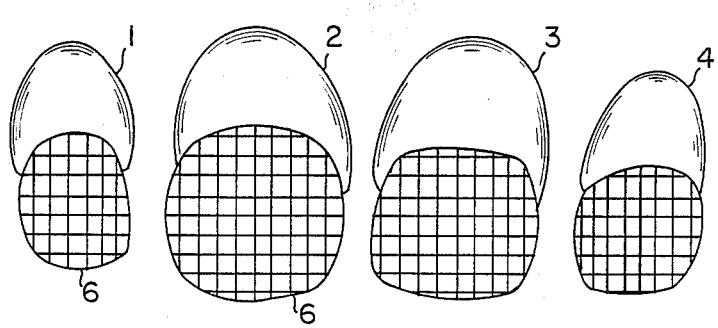
FIG. 3 is a front view of fabric-resin complex placed on the labial surfaces of the teeth.

FIG. 3 shows a fabric-resin complex 6, placed on the labial surface of the teeth 1 to 4.

Figure 4:
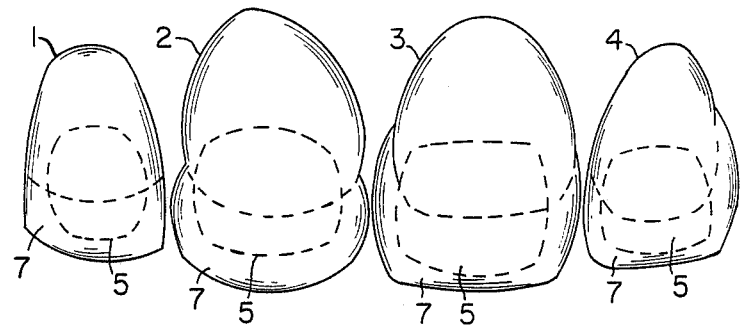
FIG. 4 is a front view of fabric-resin matrix totally enveloped in bonding resin.

FIG. 4 shows the fabric-resin complex, 5 or 6, enveloped in bonding resin 7.

Figures 5A, 5B, 5C:
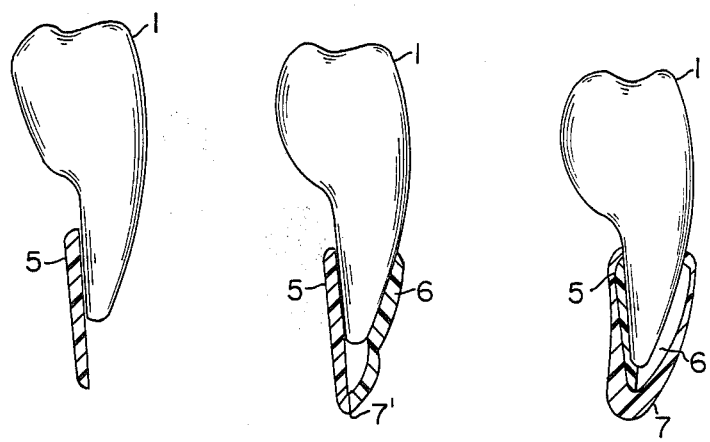
FIGS. 5A–C show side views, partly in section of a tooth illustrating the process of the invention.

FIG. 5A shows a side view of the fabric-resin complex 5 placed on the lingual surface.

FIG. 5B shows the fabric-resin complexes 5 and 6, mounted on the lingual and labial surfaces. FIG. 5B also shows the complexes 5 and 6 being joined together at point 7, for the purpose of lengthening the tooth 1.

FIG. 5C shows the fabric-resin matrix 5, 6, totally encased in bonding resin 7.

REFERENCES

Black, J. B.: Esthetic restoration of tetracycline stained teeth, J.A.D.A., 1982, 104: 846–852

Buonocore, M. G.: Retrospections on bonding, Dent. Clinics of N. Amer., Saunders, 1981 25 (2): 243

Buonocore, M. G.: A simple method of increasing the adhesion of acrylic filling materials to enamel surfaces, J. Dent. Res., 1955

Boyer, D. B. et al: Build-up and repair of light-cured composites: bond strength, J. Den. Res, 1984, 63 (10): 1241–1244

Chan, K. C. and Boyer, D. B.: Repair of conventional and microfilled composite resins, J. Prosth. Dent, 1983, 50 (3): 345–50

Golub, J. E.: The role of the cosmetic dentist, New York State Dental Journal, 1985, (483–485)

Gwinnett, A. J.: Acid etching for composite resins, Dent. Clinics of N. Amer., 1981, 25 (2): 275

Gwinnett, A. J.: Personal communication

Hendell, D.: Lecture First Dist. Dent. Soc. Continuing Education Program 1985, 1986

Jordan et al: Esthetic Composite Bonding

Pollack, B. F.: Personal communication

It is claimed:

1. The process for reshaping teeth as follows:
   (a) apply soft orthodontic wax to approximate and mock-up the final restoration, a study model of the waxed mock-up is optional,
   (b) pumice the teeth, etch them on all surfaces and then use standard lavage and drying techniques,
   (c) cut cloth in ½ inch lengths measured as wide as the proximal incisal corners, less about ½ mm from each edge, cut two for each tooth and hold aside, affix the cloth about half way up the tooth even for a 1 or 2 mm, extension, for bruxers, even the tiniest extension requires a cloth wrap, the cloth ribbons can actually be any length, incisal excess to be cut later, the cloth extending to within ½ mm of the final bonded length,
   (d) apply light-cured bonding liquid to the enamel surface and cure,
   (e) apply a non-light cured luting agent,
   (f) place a cellophane strip loosely adjacent to the lingual surface wrapping labially through the two interproximals, place autocured adhesive paste on the ligual enamel and onto the sides, wet the cloth thoroughly with the paste, compress the parts together with the strip insuring that the extended cloth is following the imaginary inclined plane of the lingual surface of the tooth, remove any paste adhesive which spills onto the labial surface,
   (g) apply a new mix of adhesive paste on the labial enamel and on a second piece of cloth, compress again with a clear plastic strip against the hardened lingual cloth-resin complex,
   (h) once set, reduce the cloth structure with a dry medium diamond stone to within ½ millimeter of the ultimate bonded length and width and check the occlusion,
(i) roughen cloth-resin material which appears shiny and add light cured bonding adhesive to the cloth structure and to the remaining enamel surface and cure it,
(j) add the composite resin, choosing a macrofill for the lingual surface for strength and a microfill for the labial surface for polish and luster,
(k) sculpt and finish normally, the outer bonding composite resin should envelope the cloth entirely and should be firmly attached to the labial, lingual and proximal enamel surfaces, as well as to the cloth-resin complex,
(l) polish and finish.

2. The process as in claim 1 adding the following step after step "f": f(1) place a bonding resin, preferably a macro type at the incisal edge and slightly onto the labial surface to fill in the space.

3. The process as in claim 1, wherein the cloth is one of the group including silk and nylon.

* * * * *